(12) United States Patent
Stringer

(10) Patent No.: US 6,558,664 B1
(45) Date of Patent: May 6, 2003

(54) CHONDROCYTE CELL-LINES

(75) Inventor: Bradley Michael John Stringer, Cardiff (GB)

(73) Assignee: Cell Factors plc, Cambridge (GB)

( * ) Notice: Subject to any disclaimer, the term of this patent is extended or adjusted under 35 U.S.C. 154(b) by 0 days.

(21) Appl. No.: 09/397,789

(22) Filed: Sep. 16, 1999

Related U.S. Application Data (63) Continuation of application No. 08/849,677, filed on Jun. 13, 1997, now abandoned.

(30) Foreign Application Priority Data

Dec. 13, 1994 (GB) .............................................. 9425071

(51) Int. Cl.$^7$ ................................................. C12N 5/00
(52) U.S. Cl. ....................... 424/93.7; 435/366; 435/372
(58) Field of Search ................................. 435/366, 372; 424/93.7

(56) References Cited

FOREIGN PATENT DOCUMENTS

WO    WO 94/09118    4/1994

OTHER PUBLICATIONS

Clark(1981), Miscellaneous Staining in Staining Procedures Eds., Williams an Wilkins. publ Baltimore, New York.
Frazer(1994), Osteoarthritis and Cartilage, 2:235–45.
Mallein–Gerin et al. (1993) Proc. Natl. Acad. Sci. USA: 3289–93.
Gowen(1984), Biochim. Biophys. Acta, 797: 186–93.
Hollander(1994), J. Clin Invest., 93: 1722–32.
Iwamoto et al. (1993) J. Biol. Chem. 268:9645–52.
Jikko(1993), Dev. Biol., 156:372–80.
Kato(1988), Proc. Natl. Acad. Sci. USA, 85:9552–6.
Leboy(1989), J. Biol. Chem., 264:17281–6.
Lefebvre et al. (1995) J. Cell Biol. 128:239–45.
Pacifici(1991), Exp. Cell Res., 912:266–70.
Quarto et al. (1992) Developmental Biol. 149:168–76.
Sandell(1988), Tiss. Res., 17:11–22.
Stephens(1992), J. Cell Sci., 103:1111–6.
Takigawa et al. (1991) Int. J. Cancer 48:717–25.
Wareham(1987), Nature, 327: 725–7.
Kirsch et al., (1991) FEBS Letters 294:149–54.
Horton et al., (1988) Experimental Cell Res. 178:457–68.

*Primary Examiner*—Jean C. Witz
(74) *Attorney, Agent, or Firm*—Klauber & Jackson

(57) ABSTRACT

The invention relates to chondrocytes and chondrocyte cell-lines for use especially in studying arthritic conditions and also for developing skeletal tissue for use in repair and/or replacement surgery. The use of articular chondrocyte cell-lines which mineralize calcium to determine potentially beneficial therapeutic agents is disclosed. Further, the means for producing such cell-lines is also disclosed as well as the characteristics of such cell-lines. The use of hypertrophic chondrocyte cell-lines to produce matrix tissue is also disclosed. Further means of producing hypertrophic chondrocyte cell-lines is also disclosed as well as the charatictics of such cell-lines.

11 Claims, 8 Drawing Sheets

3 CHONDROCYTE CLONES

FIG. 6

CHONDROCYTE CELL-LINES

This Application is a Continuation, of application Ser. No. 08/849,677, filed Jun. 13, 1997, now abandoned, which is a 371 of PCT/GB95/02497 filed Oct. 25, 1995.

The invention relates to Chondrocytes and Chondrocyte Cell-Lines for use, particularly but not exclusively, for studying arthritic conditions.

In addition, the invention relates to chondrocytes which may be of particular advantage in the development of new biomaterials for use in replacing skeletal tissues such as hips and joints.

Arthritis is characterised by inflammation of the joints and thus an inflammation of cartilage tissue. Cartilage is made from materials secreted by cells, and specifically Chondrocytes, into extracellular space. Two of the most prominent materials to be secreted by cells are collagen and mucopolysaccharides. Mucopolysaccharides are large molecular weight sugar molecules comprising carbohydrate chains which exists as repeating disaccharides. One of the two sugars is always an amino sugar, either N-acetyl-glucosamine or N-acetyl-galactosamine. In most cases, mucopolysaccharides exist in combination with proteins and thus form proteoglycans.

Collagen is fibrous in structure whereas mucopolysaccharides are amorphous in appearance and extremely viscous and can thus occupy large volumes for a given weight of material. In many cases collagen and proteoglycans interact with one another to form a variety of extracellular structures. These structures appear to be self-organising; there is no evidence of enzymes or other materials which bring about their polymerisation, interaction or orientation. For example, a typical collagen proteoglycan found in cartilage may consist of a central filament of hyaluronic acid several micro meters long having bound thereto, at regular intervals, link proteins. Long core proteins bind to the link proteins and branching from the core proteins at regular intervals are mucopolysaccharides such as chondroitin sulphate and keratan sulphate. Thus extracellular matrix materials organise themselves to form cartilage.

Bone formation is characterised by calcification in the region of hypertrophic chondrocytes. Whilst vascular invasion is important for mineralisation in vivo, it is clear that initiation of calcification can be independent of vascularization, since hypertrophic chondrocytes can spontaneously mineralise their matrix in vitro in the absence of exogenous phosphate. However, adult articular cartilage does not normally calcify, except at its junction with subchondral bone where the calcification forms a characteristic tide-mark. It is therefore interesting to note that chondrocalcinosis, the pathological calcification of articular cartilage by calcium pyrophosphate, which occurs in different regions of articular and other cartilage, increases in prevalence with age and may be associated with osteoarthritis.

It therefore follows that understanding the mechanisms associated with osteoarthritis should involve an understanding of the mechanisms associated with calcification of articular cartilage. However, there are no cell models for this investigation. Rather, existing cell models employ the use of growth plate chondrocytes, that is to say chondrocytes which mineralise calcium in order to produce bone tissue. Using this chick cell model it has been possible to show that chick growth plate chondrocyte cell layers become mineralised in the presence of ascorbate or of beta-glycerophosphate (1). The effects of ascorbate are associated with an increase in the synthesis of alkaline phosphatase and type X collagen, though it is not clear if they are both essential for calcification to occur. Beta-glycerophosphate acts independently of regulation of these two molecules, presumably by providing a rich source of exogenous phosphate for nucleation. Other workers have developed a pellet culture system for rabbit growth plate chondrocytes in which there is synthesis of alkaline phosphatase and type X collagen as well as calcification in cultures with ascorbate (2). A separate study (3) suggests that the effects, of ascorbate may be species-specific, highlighting the need for a human chondrocyte model system if human disease processes are to be studied.

No studies to date have shown calcification of matrix in vitro by articular chondrocytes. Workers have compared rabbit articular and growth plate chondrocytes and found that in high-density cultures the growth plate chondrocytes produce alkaline phosphatase and incorporate calcium into the cell layers, whereas articular chondrocytes do not (4). However, two studies have demonstrated that chick (5) or human (6) articular chondrocytes can express type X collagen and alkaline phosphatase in long-term cultures, but, there is no evidence for calcification of cell layer matrix in either study.

Other workers have described in International Patent Application WO9409118, the closest prior art, how a human chondrocyte cell-line can be produced by transfecting juvenile primary chondrocytes using an SV40 oncogene. The chondrocytes express Type II collagen a specific matter for articular chondrocytes. However, there is no reference to matrix calcification of matrix using these cell-lines.

It can therefore be seen that existing in vitro models of calcification rely on long-term cultures of animal growth plate chondrocytes. There is currently no model of human chondrocyte calcification.

We have surprisingly found that mature articular chondrocytes and immortalised articular chondrocyte cell-lines provide an extracellular matrix that rapidly calcifies. By the term mature, we mean chondrocytes from an elderly individual such as an individual of an age likely to development osteoarthritis such as, but not limited to, an individual over the age of 50, and more preferably 65. Or, alternatively, chondrocytes grown in vitro of functionally equivalent age.

Our finding therefore represents a valuable opportunity for the study of mechanisms associated with calcification of articular cartilage and also for the regulation of said calcification. We expect that our articular chondrocyte cell-lines will have both academic and commercial value in that they will not only facilitate a greater understanding of calcification that may be associated with the osteoarthritic condition but they will also serve as valuable tools for the development of therapeutic agents to treat such a condition.

We are unable to explain our findings but we speculate as follows. During development chondrocytes are typically committed to one of two lineages. The first concerns the production of bone and thus the differentiated chondrocytes mineralise calcium. The second lineage concerns the production of cartilage tissue and thus the differentiated chondrocytes do not mineralise calcium. It may be that there is some plasticity in the determination of lineage and, for example, this may be related to demethylation of DNA with ageing.

Thus as articular chondrocytes age the control mechanisms that prevent calcium mineralisation operate less effectively and surprisingly chondrocytes of the articular cartilage lineage actually mineralise calcium.

Our findings thus suggest that, contrary to previous expectations, it is possible to provide a human cell model for arthritis. The cell model can be provided using either mature or immortalised articular chondrocytes and ideally cell-lines pertaining thereto.

According to a first aspect of the invention there is therefore provided an articular chondrocyte which mineralises calcium.

Preferably there is provided a plurality of chondrocytes which are arranged in pellet form.

Preferably said chondrocyte and chondrocytes are derived from a mature individual, and ideally from such an individual suffering from or having a predisposition for arthritis. Alternatively, said chondrocyte and chondrocytes are of foetal origin and preferably human foetal origin. More preferably still said chondrocyte and chondrocytes are mature as herein defined.

Preferably further still there is provided cell-lines of such chondrocytes.

In preferred embodiments of the invention said cell-lines are of human origin and ideally comprise an oncogene and ideally a temperature sensitive oncogene so that at a first permissive temperature an active oncogene product is expressed and at a second non-permissive temperature expression of the active oncogene product is prevented. We have found that use of such an oncogene product provides for a cell-line which at the non-permissive temperature shows an increase in type II collagen expression—a marker for the fully differentiated phenotype.

Ideally the oncogene is a temperature sensitive mutant of the immortalising oncogene SV40-T.

We are unsure, at this stage, whether calcium mineralisation by articular chondrocytes is directly responsible for osteoarthritis, or alternatively, whether calcium mineralisation by articular chondrocytes is an indicator of a yet unidentified condition or marker which is responsible for osteoarthritis. In either case, the cell-lines of our invention represent suitable cell models for further investigation.

As mentioned above, we are further unsure, at this stage, about the nature of the mechanisms which lead to calcium mineralisation by articular or hypertrophic chondrocytes. Other workers have suggested that there exists age related reactivation of genes (7). Thus as we speculated above it may be that a process of de-differentiation gives rise to osteoarthritis. It may be that genes which are typically inactive during life are switched on with ageing and are thus responsible for the aberrant phenotype of the mature articular chondrocyte.

The above speculation is provided for the purpose of edification only. It is not intended that the application should be limited by any of the above speculations, rather the speculations are provided for the purpose of comprehension.

There are obvious advantages to be derived from the use of in vitro cell models that mimic the arthritic condition. But, in addition we have produced chondrocyte cell-lines from foetal tissue which express type X collagen, a marker of hypertrophic chondrocytes. Such chondrocytes are known to mineralise calcium and therefore once the phenotype of these cells was determined the existence of mineralisation was less surprising. However, it is of note that no one has ever made a human hypertrophic chondrocyte cell-line before, despite its obvious advantages in understanding the mineralisation process symptomatic of the arthritis condition. Moreover, no one has thought to make such a cell-line for the study and/or production of joint matrix tissue for use in skeletal repair and/or replacement studies and/or surgery. We therefore also present herein knowledge of, and methods relating to, the production of a human hypertrophic chondrocyte cell-line.

According to a second aspect of the invention there is provided a human hypertrophic chondrocyte cell-line.

In a yet a further preferred embodiment of the invention said cell-line is of human foetal origin and also ideally comprises an oncogene and ideally a temperature sensitive oncogene so that at a first permissive temperature an active oncogene product is expressed and at a second non-permissive temperature expression of the active oncogene product is prevented. We have found that use of such an oncogene product provides for a cell-line which at the non-permissive temperature shows type X collagen expression, a marker for hypertrophic chondrocytes. Thus alternative cell-lines derived from human foetal tissue which mineralise calcium can be provided.

According to yet a further aspect of the invention there is provided a method for producing articular chondrocyte cell-lines, which method comprises:
a) immortalising at least one mature human articular chondrocyte cell using an immortalising agent; and
b) culturing said immortalised cell in order to produce a population of human articular chondrocyte cells.

Preferably the immortalising agent is an oncogene and more preferably still a temperature sensitive oncogene which at a non-permissive temperature results in enhanced expression of the phenotypic characteristics of the chondrocyte.

In a preferred embodiment of the invention immortalisation is achieved using conventional transfection techniques and preferably the immortalising agent is an immortalising gene such as an oncogene and more preferably still a temperature sensitive mutant of the immortalising oncogene SV40-T.

Ideally said method further involves culturing said immortalised cell at the non-permissive temperature of the oncogene.

According to a yet further aspect of the invention there is provided a method for producing hypertrophic chondrocyte cell-lines, which method comprises:
a) immortalising at least one human foetal chondrocyte cell using an immortalising agent; and
b) culturing said immortalised cell in order to produce a population of human foetal-derived chondrocyte cells.

Preferably the immortalising agent is an oncogene and more preferably still a temperature sensitive oncogene which at a non-permissive temperature results in enhanced expression of the phenotypic characteristics of the chondrocyte.

In a preferred embodiment of the invention immortalisation is achieved using conventional transfection techniques and preferably the immortalising agent is an immortalising gene such as an oncogene and more preferably still a temperature sensitive mutant of the immortalising oncogene SV40-T. More preferably still said transfection is undertaken using retroviral temperature sensitive oncogene transduction.

Ideally said method further involves culturing said immortalised cell at the non-permissive temperature of the oncogene.

According to a yet further aspect of the invention there is provided chondrocytes, or at least one chondrocyte cell-line, in accordance with the invention for use in developing therapeutic agents designed to treat arthritis.

According to a yet further aspect of the invention there is provided a method for developing therapeutic agents designed to treat arthritis comprising:
a) exposing chondrocytes, or at least one chondrocyte cell-line, in accordance with the invention to at least one test agent; and b) observing the nature of the response to said test agent.

In a preferred method of the invention said observation involves an assessment of the amount of calcium mineralisation associated with said chondrocytes or said chondrocyte cell-lines.

According to an alternative aspect of the invention there is provided hypertrophic chondrocytes, or at least one hypertrophic chondrocyte cell-line, for use in providing joint matrix tissue.

According to an alternative aspect of the invention there is provided a method of producing joint matrix tissue for use in repair and/or replacement of damaged tissue comprising:

a) providing a hypertrophic chondrocyte cell-line;

b) culturing said cell-line under conditions that promote matrix growth; and c) harvesting said cells and/or said matrix tissue and/or selected parts thereof.

The invention will now be described by way of example only with reference to the following examples, wherein.

IMMORTALISATION OF ARTICULAR CHONDROCYTES

Reference 13 is provided as a general method of preparing human articular chondrocytes for primary culture, but any published method will suffice. In short chondrocytes from sections of mature human tibial and femoral condyles from patient biopsies were enzymatically digested (14) and placed in tissue culture flasks (Costar Ltd. UK) in Eagle's minimum essential medium (Gibco Ltd. UK) containing antibiotics and L-glutamine as well as 10% heat inactivated foetal bovine serum. Cultures were maintained in a humidified atmosphere of 5% $CO_2$ at 37° C. and medium changed at regular intervals. The adherent cell population was then transfected with a temperature sensitive mutant of the simian virus-40 derived large tumour (T) antigen using retroviral transduction, Any standard method of transfection of this sequence (along with linkage to an appropriate promoter to drive its expression eg LTR promoter) would suffice, such as calcium phosphate DNA precipitation, electroporation or micro-injection, but retroviral transduction was chosen for its simplicity of use.

Immortalisation of Human Foetal Tissue

Foetal rib or femur tissue was taken at 7–9 weeks of gestation and placed in tissue culture flasks (Costar Limited, UK) in Eagle's minimum essential medium (Gibco Co Limited, UK) containing antibiotics and L-glutamine as well as 10% heat in activated foetal bovine serum. Cultured cells were maintained in a humidified atmosphere at 5% $CO_2$ and 37° C. and medium changed at regular intervals (2–3 days). As is usual for primary cultures of resected tissue, cells within the sample move out from the body of the tissue, adhere to the flask surface, and replicate, potentially, to cover the whole surface of the tissue culture dish. After an initial period of, say, 2 weeks in primary culture. The cell population was transfected with a temperature sensitive mutant of the simium virus-40 derived large tumour (T) antigen using retroviral transduction.

Culturing of the Immortalised Cells in Order to Produce a Homogenous Population of Cells In short, amphotropically packaged retroviral particles comprising this construct and a resistance marker to geneticin, G418 (kindly donated by Dr M O'Hare, Institute of Cancer Research, Royal Marsden Hospital, Lincoln's Inn, Sutton, Surrey, alternatively, essentially the same construct expressing a temperature sensitive mutant of the SV40-T oncogene was kindly donated by Professor Phil Gaillimore, CRC Laboratories, University of Birmingham, UK) was added to the medium together with polybrene (Sigma Chemicals) to a final concentration of 0.8 mg/ml. The viral titre was adjusted to give a low transduction efficiency of 0.0002% producing an average of 20 immortalised cell colonies per flask, each colony derived from a single cell. Two hours after virus addition, the culture medium was replaced with fresh medium. Cultures were maintained at 33° C., the permissive temperature for the active form of the SV40-T oncogene product. Five days after transduction, geneticin was added to the medium (0.4 mg/ml) for a further 10 days to eradicate cells which had not incorporated the retroviral vector.

Differentiation of Said Cells

Between 14–20 days after transduction, individual colonies of replicating cells were identifiable. Clones were selected on the basis of being well separated from other replicating colonies, the cells in each colony numbering between 100–1000 cells. These were picked by ring cloning and expanded up to near confluence in 75 $cm^2$ flasks (Costar, UK Ltd) which equated to approximately 22 divisions from a single cell, prior to freezing stocks down in aliquots. Samples were also used for cell characterisation and to determine that they possessed the ability to express articular chondrocyte specific markers. Expression was effected by exposing the cells to the oncogene's non-permissive temperature (39° C.). Clones were derived from the routine method of single cell expansion.

Figure 1:
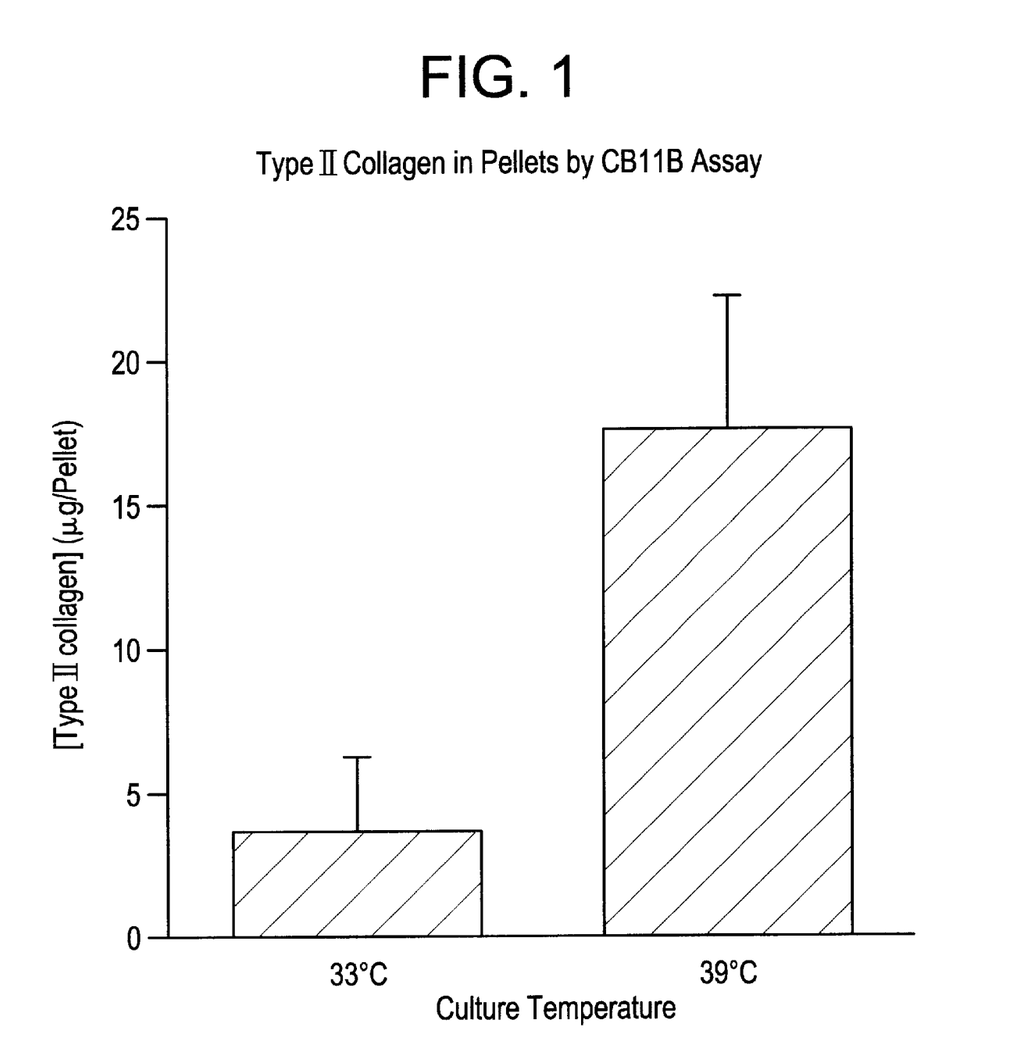
FIG. 1 shows an upregulation of Type II collagen expression in human articular chondrocytes.

Experiments to Show Functional Characteristics of the Differentiated Articular Chondrocyte Cell-Line A specific marker of articular chondrocytes is the ability to express Type II collagen (8). The cells of our invention were therefore investigated in order to show Type II collagen expression. Immortalised human chondrocytes were exposed to 39° C., the non-permissive temperature of the oncogene, after pellet culture (9,10) for six weeks. FIG. 1 shows the mean of 6 pellets incubated at either the permissive temperature of 33° C. or the non-permissive temperature of 39° C. The error bars represent the standard deviation. FIG. 1 clearly shows an upregulation of Type II collagen expression at the non-permissive temperature of 39° C. This data indicates that our cell-lines comprise differentiated functional articular chondrocytes.

Extracellular Calcification

Figure 2A:
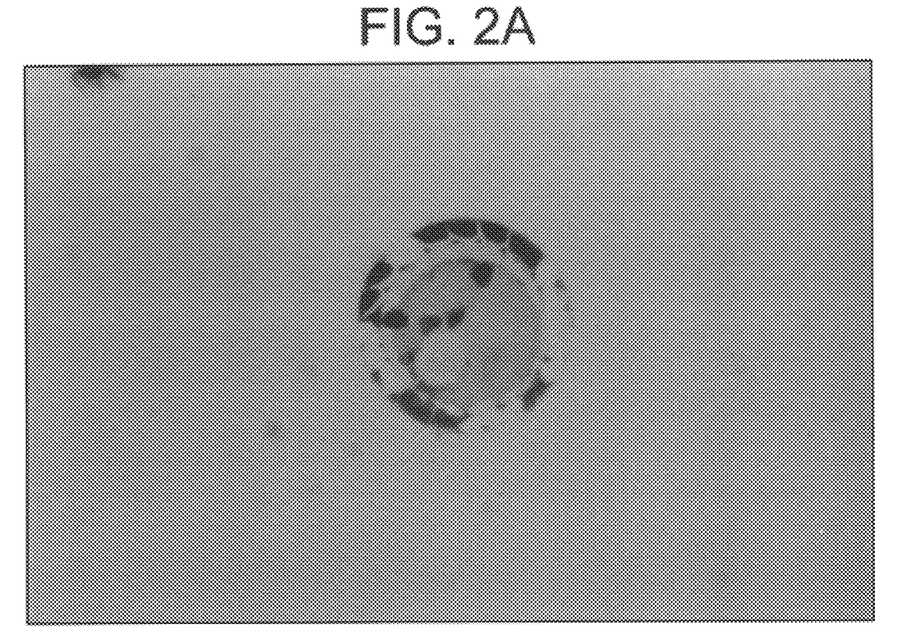
FIG. 2 shows the extracellular calcification achieved by these cells using a standard histological procedure (Von Kassa staining, 11) for the identification of calcification in tissue matrix.
Figure 2B:
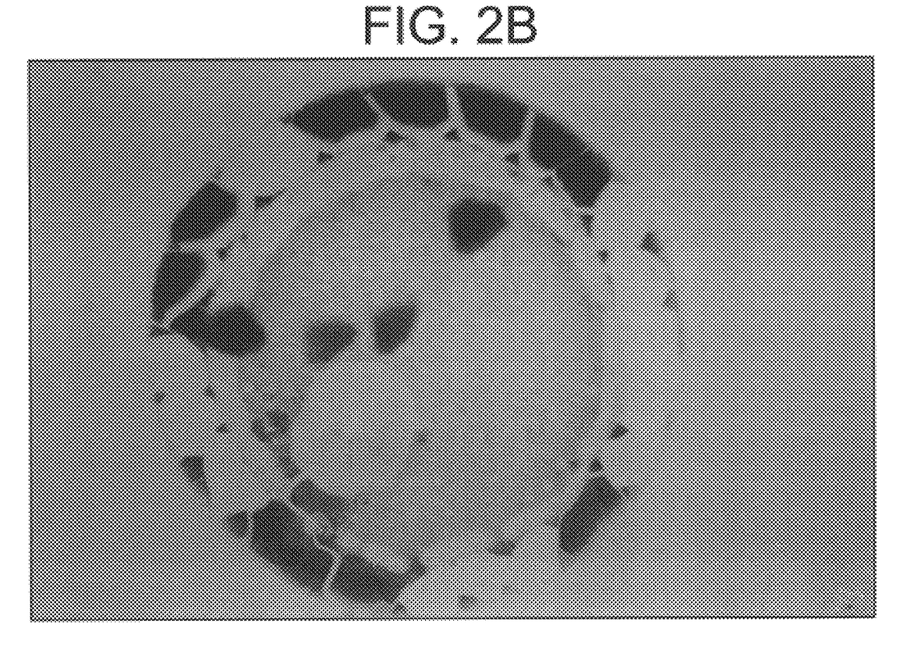
Figure 2C:
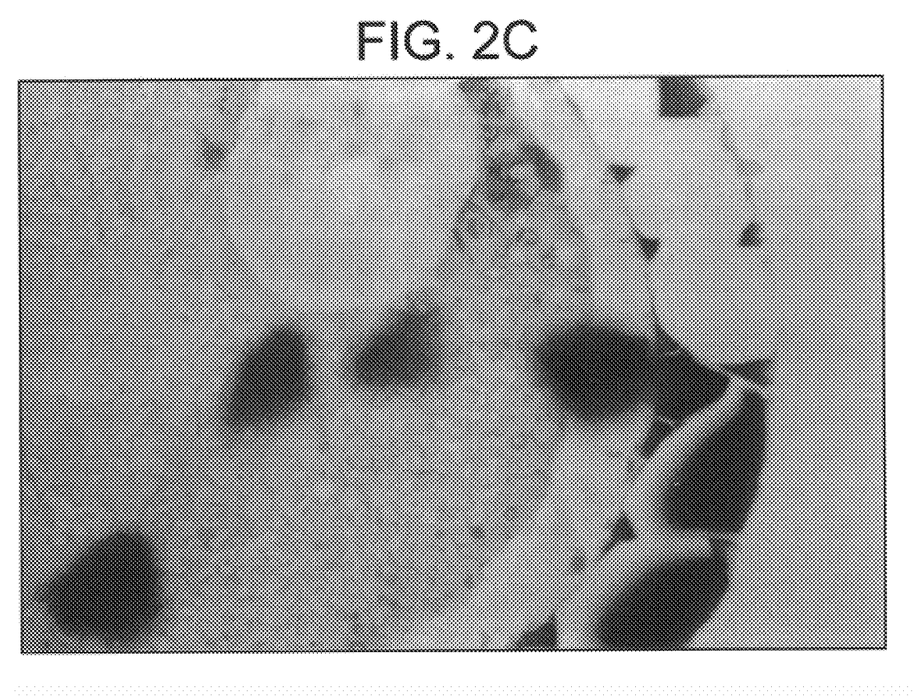
Figure 3A:
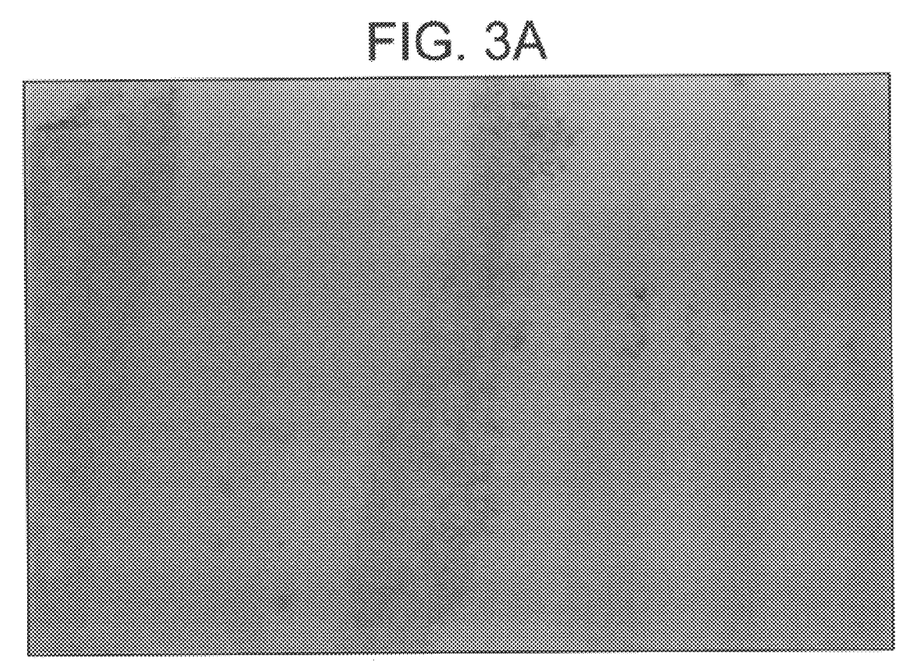
FIG. 3 depicts the immunocytochemically localised type X collagen (12) in these cells suggesting the expression in-vitro of characteristics expected of hypertrophic chondrocytes.
Figure 3B:
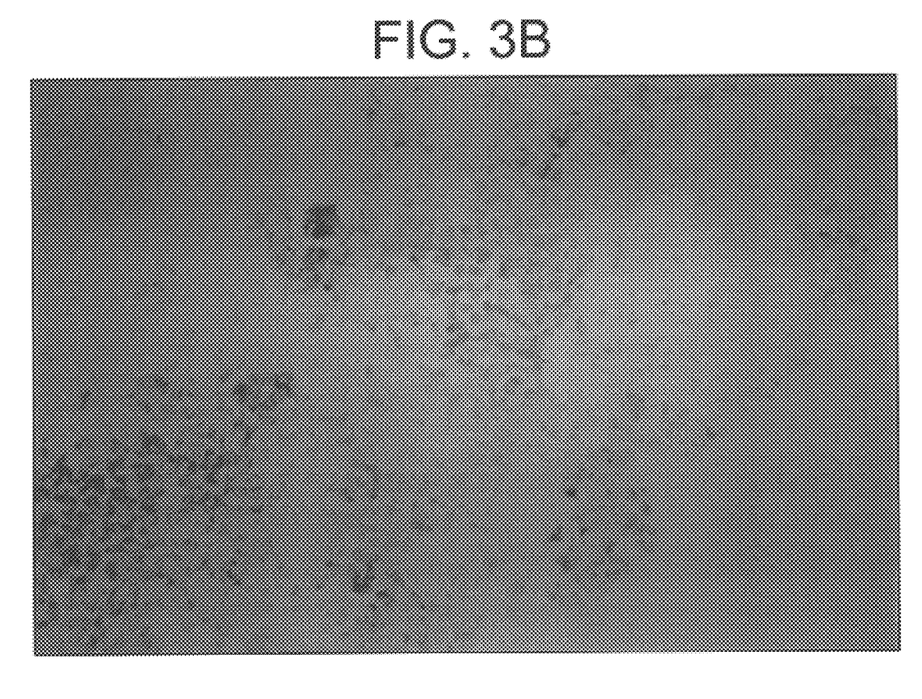
Figure 3C:
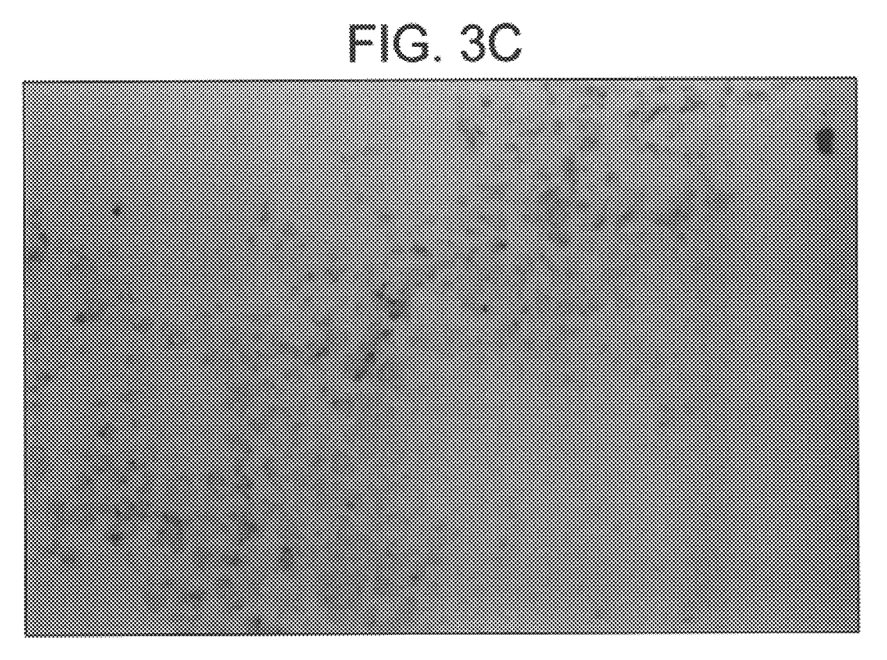

FIGS. 2 and 3 show the extracellular calcification achieved using cells in accordance with the invention.

Specifically, FIG. 2 shows a standard histological procedure (Von Kossa Staining, 11) for the identification of calcification in tissue matrix. The dark areas (Von Kossa Positive Staining) represent the calcified matrix produced by these articular chondrocytes, this being separated by the likely stained or unstained chondrocyte cells in the culture. FIG. 3 is included to show immunocytochemically localised type X collagen (12) in these cells suggesting the expression in-vitro of characteristics expected of hypertrophic chondrocytes. This data tends to suggest that the cells of the invention may have de-differentiated in order to show characteristics associated with hypertrophic chondrocytes.

Longevity of the Human Articular Chondrocyte Cell-Line

Using the method of the invention we have surprisingly found that our human articular chondrocyte cell-lines successfully differentiate to produce functional cells with articular chondrocyte characteristics. The cells continue to survive and have passed through more than 60 divisions over a period of 2 years producing $10^{18}$ cells from a variety of clones. The cell-lines continue to survive and moreover the cells of the line continue to show functional characteristics typical of the tissue type of the differentiated cell. Furthermore we have been able to produce immortalised human articular chondrocyte cell-lines comprising differentiated cells that surprisingly mineralise calcium.

Experiments to Show Functional Characteristics of the Differentiated Hypertrophic Foetal-Derived Chondrocyte Cell-Line A specific marker of hypertrophic chondrocytes is the ability to express type X collagen. The cells of our invention were therefore investigated in order to show type X collagen expression. All our foetal-derived chondrocytes expressed this cell marker and furthermore tests were undertaken and it was concluded that type I collagen was not expressed in these cells clearly showing that they were not of osteoprogenitor origin.

Figure 4:
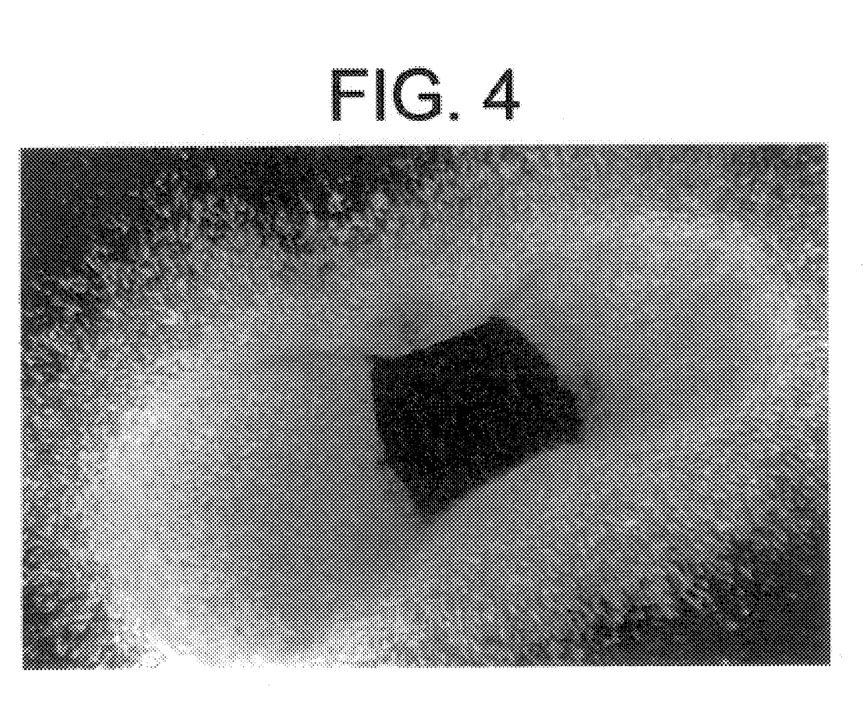
FIG. 4 shows a femur derived from a human foetus which has been cultured for 14 days.

FIG. 4 shows a femur derived from a human foetus of 7–9 weeks gestation and of approximately 600 micrometers in length. The femur has been cultured in the afore described culture medium for a period of 14 days to allow the outgrowth and expansion of replicating cell populations as would be the case for any primary cell culture. No prior treatment with enzyme(s) is required in this instance, however, to help in cell retrieval. Cell expansion for 14 days was performed prior to retroviral temperature sensitive oncogene transduction.

Extracellular Calcification

Figure 5:
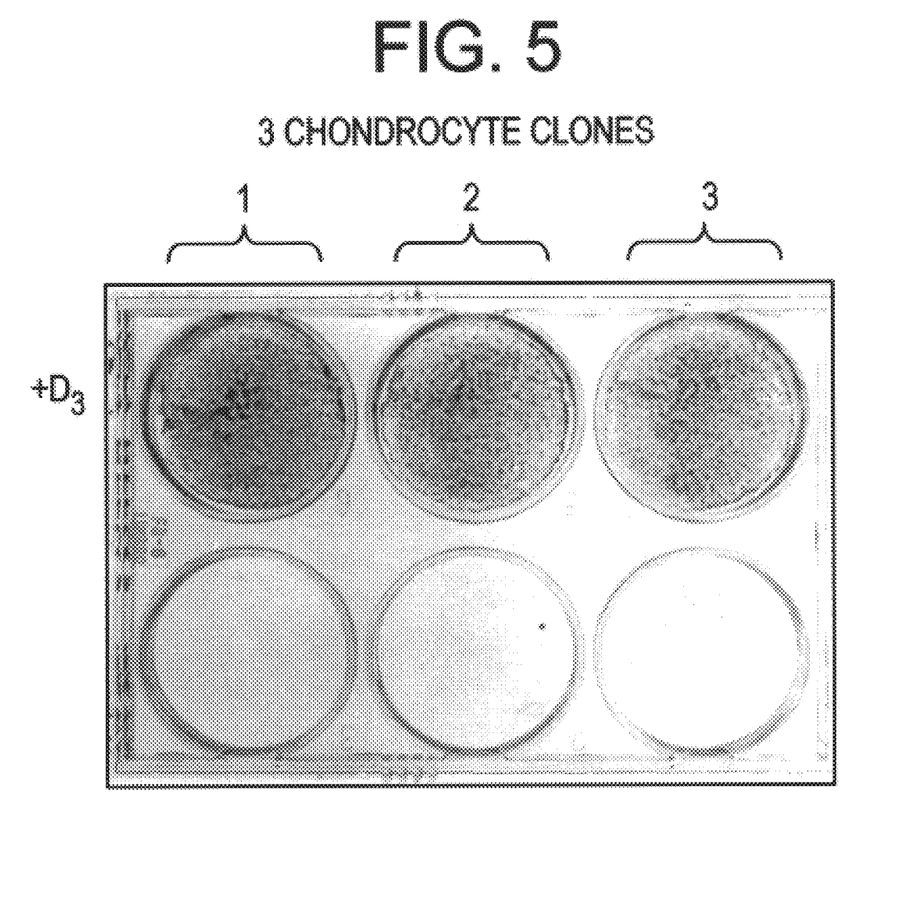
FIG. 5 shows 3 chondrocyte cell-lines cloned from foetal femur when cultured either in the presence of 1,25(OH)2D3 (top row) or in the absence of 1,25(OH)2D3.

The immortalised foetal-derived hypertrophic chondrocytes were also responsive to 1,25(OH)2D3 and expressed high levels of alkaline phosphatase activity, two further markers of the hypertrophic chondrocyte-like phenotype. When the cells are left in monolayer culture for 10–14 days at 39° C., the oncogene's non-permissive temperature, and in the absence of added β-glycerophosphate the cultures mineralise. This can be clearly seen in FIG. 5 as it shows three chondrocyte cell-lines cloned from foetal femur after retroviral transduction with a temperature sensitive oncogene. Each cell-line has a basal level of alkaline phosphatase activity and some type X collagen expression. If the cells are plated and incubated at the oncogene's non-permissive temperature, and in the presence of 1,25(OH)2D3, top row, each clone actively mineralises calcium as illustrated by the standard histological procedure of Von Kossa staining as afore described. Cells plated and incubated at the oncogene's non-permissive temperature in the absence of 1,25 (OH)2D3, bottom row, do not actively mineralise calcium.

Figure 6:
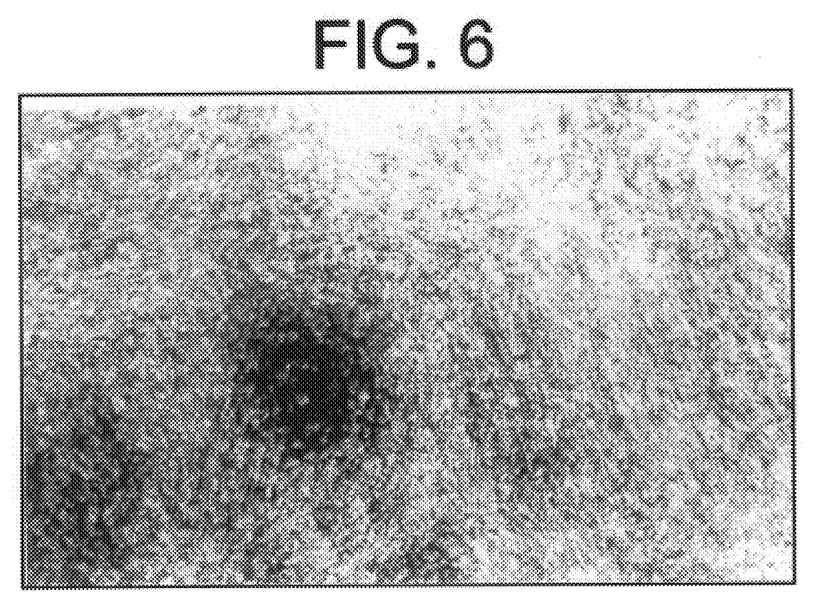
FIG. 6 shows an actively mineralising monolayer culture of a chondrocyte cell-line derived from human foetal cells.

Finally, FIG. 6 shows, again using Von Kossa staining, an actively mineralising monolayer culture of a chondrocyte cell-line derived from human foetal cells. Dark patches represent the mineralised matrix which develops and overlays the cultured cells which adhere the surface of the culture dish.

We have therefore clearly demonstrated that it is possible to produce articular chondrocyte cell-lines—either derived from mature adult tissue, or alternatively, immortalised younger human tissue—which mineralise calcium. Our cell-lines thus have use in identifying agents which affect the mineralisation of calcium by these tissues. We have also demonstrated that it is possible to provide human hypertrophic chondrocyte cell-lines for use as afore and also for use in the development of biomaterials for use in any number of applications but particularly for use in developing materials for use in joint replacement.

REFERENCES

1. Leboy P. S., L. Vaias, B. Uschmann, E. Golub, S. L. Adams and M. Pacifici 1989. Ascorbic acid induces alkaline phosphatase, type X collagen, and calcium deposition in cultured chick chondrocytes. *J Biol. chem.* 264:17281–17286.
2. Kato Y., M. Iwamoto, T. Koike, F. Suzuki, and Y. Takano. 1988. Terminal differentiation and calcification in rabbit chondrocyte cultures grown in centrifuge tubes: Regulation by transforming growth factor β and serum factors. *Proc. Natl, Acad, Sci, USA* 85:9552–9556
3. Sandell L. J., and J. C. Daniel. 1988. Effects of ascorbic acid on collagen mRNA levels in shortterm chondrocyte cultures. *Tiss. Res.* 17:11–22.
4. Jikko A., T. Aoba, H. Murakami, Y. Takano, M. Iwamoto and Y. Kato. 1993. Characterisation of the mineralisation process in cultures of rabbit growth plate chondrocytes. *Dev. Biol.* 156:372–380.
5. Pacifici M., E. B. Golden, S. L. Adams and I. M. Shapiro. 1991. Cell Hypertrophy and type X collagen synthesis in cultured articular chondrocytes. *Exp. Cell Res.* 912:266–270.
6. Stephens M., A. P. L. Kwan, M. T. Bayliss and C. W. Archer. 1992. Human articular surface chondrocytes initiate alkaline phosphatase and type X collagen synthesis in suspension culture. *J. Cell. Sci.* 103:1111–1116.
7. Wareham K. A., M. F. Lyon, H. Glenister and E. D. Williams. 1987. Age related reactivation of an X-linked gene. *Nature* 327:725–727.
8. Hollander A. P., Heathfield T. F., Webber C, Iwata Y, Bourne R, Rorabeck C and Poole A. R., 1994. Increased damage to type II collagen in osteoarthritic articular cartilage detected by a new immunoassay. *J Clin. Invest.* 93:1722–1732.
9. Kato Y, Iwamoto M, Koike T, Suzuki F and Takano Y 1988. Terminal differentiation and calcification in rabbit chondrocyte cultures grown in centrifuge tubes: Regulation by transforming growth factor-b and serum factors. *Proc. Nat. Acad. Sci (USA)* 85:9552–9556.
10. Jikko A, Aoba T, Murakami H, Takano Y, Iwamoto M and Kato Y, 1993. Characterisation of the mineralisation process in cultures of rabbit growth plate chondrocytes. *Dev. Biol.* 156:372–380.
11. Clark G, 1981. Miscellaneous Stains in Staining Procedures Eds. Williams and Wilkins. publ Baltimore, N.Y.

12. Stephens M, Kwan A. P. L., Bayliss M. T., and Archer C. W., 1992. Human articular surface chondrocytes initiate alkaline phosphatase and type X collagen synthesis in suspension culture. *J. Cell. Sci.* 103:1111–1116.
13. Frazer A, Bunning R, Thavarajah M, Seid J and Russell R. G. G., 1994. Studies on type II collagen and aggrecan production in human articular chondrocytes in vitro and effects of transforming growth factor-b and interleukin-1b. *Osteoarthritis and Cartilage* 2:235–245.
14. Gowen M, Wood D. D., Ihrie E. J., Meats E. J., and Russell R. G. G., 1984. Stimulation by human interleukin-1 of cartilage breakdown and production of collagenase and proteoglycanase by human chondrocytes but not human osteoblasts in-vitro. *Biochim. Biophys. Acta* 797: 186–193.

What is claimed is:

1. A human hypertrophic chondrocyte cell-line wherein said cell line is of foetal origin.

2. A cell-line according to claim 1 wherein said cell-line comprises an oncogene.

3. A cell-line according to claim 2 wherein said oncogene is temperature sensitive.

4. A cell-line according to claim 2 or 3 wherein said oncogene is SV40T antigen.

5. A method for producing human hypertrophic chondrocyte cell-lines, which method comprises:
   a) immortalising at least one human foetal chondrocyte cell using an immortalising agent; and
   b) culturing said immortalised cell in order to produce a population of human foetal-derived chondrocyte cells.

6. A method according to claim 5 wherein said immortalising agent is an oncogene.

7. A method according to claim 6 wherein said oncogene is temperature sensitive.

8. A method according to claim 6 or 7 wherein said oncogene is SV40T antigen.

9. A method according to claim 7 wherein said method further involves culturing said immortalised cell at the non-permissive temperature of the oncogene.

10. A method for preparing joint matrix tissue, comprising
   a) providing hypertrophic chondrocytes or a hypertrophic chondrocyte cell line;
   b) culturing said cells or cell line under conditions that promote the growth of joint matrix tissue in said cells or cell line, and
   c) harvesting the joint matrix tissue produced by said cells or cell line.

11. A method for identifying therapeutic agents to treat arthritis comprising placing such therapeutic agents in contact with at least one hypertrophic chondrocyte or at least one hypertrophic chondrocyte cell line, and observing the response of said chondrocytes to such agents.

* * * * *